United States Patent [19]

Strawn

[11] Patent Number: Plant 5,392

[45] Date of Patent: Jan. 22, 1985

[54] MINIATURE ROSE PLANT

[76] Inventor: Leslie E. Strawn, 10422 Morningside Ave., Garden Grove, Calif. 92643

[21] Appl. No.: 473,581

[22] Filed: Mar. 9, 1983

[51] Int. Cl.[3] ..... A01H 5/00

[52] U.S. Cl. ..... Plt./7

[58] Field of Search ..... Plt./7

*Primary Examiner*—Robert E. Bagwill

[57] ABSTRACT

The subject of the present disclosure is a new and distinct variety of miniature rose plant characterized by Mars orange buds and flowers of distinctive form and further indentified by the erect, dwarf, compact plant.

1 Drawing Figure

The present invention relates to a new and distinct variety of hardy, dwarf, bush type rose plant of the miniature class; the variety being primarily characterized—as to novelty—by the Mars orange flowers, whose buds obtain an orange-brownish cast which in general effect are similar to Thanksgiving (U.S. Plant Pat. No. 2,524, expired).

The variety is further characterized by:

The unique buds and flowers.

An abundance of bloom, with flowers borne one to a stem. No side buds.

Very fragrant.

A plant which is vigorous, of upright growth habit with semi-glossy foliage with pointed leaflets; the buds and flowers being similar in form and size to the pollen parent, Sheri Anne (Miniature—U.S. Plant Pat. No. 3,826).

The plant, which has a normal height of 12 inches (30 cm), can easily be maintained at this height, or a lesser height, by occasional trimming.

A plant which grows and blooms satisfactorily both in a greenhouse or outdoors; is good for growing in pots; and provides excellent garden decoration as well as cut flowers.

The present variety of miniature rose was originated by me in my home greenhouse, located at Garden Grove, Orange County, Calif., under conditions of careful control and observation, as a cross between Dr. A. J. Verhage (Hybrid Tea—U.S. Plant Pat. No. 2,105, expired) as the seed parent and Sheri Anne (Miniature—U.S. Plant Pat. No. 3,826) as the pollen parent.

Subsequent to origination of the variety I successfully asexually reproduced it in my garden, located as foresaid, (also propagated by Pixie Treasures Rose Nursery, 4121 Propsect Ave., Yorba Linda, Orange County, Calif. by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline. All major color plate indentifications being reference to The British Colour Council Horticultural Colour Chart, except where common terms of color definitions are employed.

Type: Hardy; dwarf; bushy; upright; seedling; greenhouse; outdoors; cut flowers; garden decoration; pot plant.

Class: Miniature. Variety name: Indian Princess.

Flowers borne: Singly on upright, slender stems.

Quantity of bloom: Abundant, both outdoors and in the greenhouse.

BUD

Peduncle: Medium length, approx. 3 cm; slender and sturdy; erect; straight; reddish in color; few or many microscopic hairs; few or many glands.

Size: Before calyx breaks — small; 2 to 2½ cm.

Form: Pointed; foliaceous parts extend beyond tip of bud one half or more than its length.

Color: Green streaked with bronze. As calyx breaks — color of outside petal showing near Mars orange o13 or deeper.

BLOOM

Size: When fully open — small, averaging about 5 cm.

Petalage: Double, averaging about 20 to 25 petals, arranged symmetrically, with a few petaloids close to stamens.

Form: Cupped. As petals open symmetrically they remain in their upright position, with topmost edges of petals flairing outward. When fully open outside petals reflex back at side edges.

PETALS

Substance: Moderately thick and of good substance.

Texture: Smooth and satiny on both surfaces. Veined.

Shape:

*Outside petals.*—Broad with pointed apex; blunt base.

*Intermediate petals.*—Same as outside petals; slightly smaller; blunt base. Few have undulating edges.

*Inside petals.*—Same as outside petals; much smaller; not as wide; blunt base.

*Petaloids.*—Few, close to stamens.

COLOR

One half to three quarters open flower from a plant grown outdoors at Pixie Treasures Rose Nursery, Yorba Linda, Calif., Oct. 1982. All colors stated are close to or very near the following color definitions.

Outside petal:

*Outside surface.*—Close to or slightly deeper than Mars orange o13; deepening more in cool weather to obtain a brownish cast. Base of petal — bright golden yellow.

*Inside surface.*—Close to Mars orange o13, becoming lighter gradually to the outer edges blending to a color near Mars orange o13/3. Base of petal — bright golden yellow.

Intermediate petal:

*Outside surface.*—Close to Mars orange o13. Base yellow.

*Inside surface.*—Same as outside petal. Base yellow.

Inner petal: Same as Intermediate petal. Base same.

GENERAL COLOR EFFECT

Newly open flowers: Symmetrical arrangement of petals of Mars orange in its tones and tints with the lighter tones being to the edges of the petals and the more intense tones on the inner surface of the petals.

Three to four days open: Informal arrangement of petals. Sunlight changes color to a hue near Mars orange o13/3 or lighter with the veining of the petals retaining a deeper hue.

BEHAVIOR

Opens well in all weather. Petals tend to hang on for 6 to 7 days then fall; calyx remains and forms (usually) a hip. Flower longivity (October 1982) — plant in pot—3 to 4 days; plant in ground — 4 to 5 days; cut flowers at living room temperature — 3 to 4 days.

REPRODUCTIVE ORGANS

Stamens: Vary 50 to 60.
Filaments: Uneven lengths; 6 to 10 mm; golden.
Anthers: Tan; both introse and antrose.
Pollen: Abundant.
Pistils: Projects above disc.
Styles: Golden; several; bunched loosely; 5 mm.
Ovaries: Enclosed in calyx.
Hips: Forms hips readily.
Sepals: Permanent; spear shaped; reflexed.
Seeds: Self polinates readily with 5 or 6 seeds.

FOLIAGE

Leaves: Compound of five leaflets; 6 to 8 cm length.
Leaflets: Broad lanceolate with pointed apex; not supported by a petiolule.
Rachis: Length 4 cm; upper side grooved; under side 1 or 2 minute thorns.
Stipules: Short with slender pointed auricles flairing outward at approx. 45 degrees.
Color: Medium green; rachis may be green or bronze; serrated edges and veining may be tinted reddish brown in cool weather

GROWTH

Habit: Dwarf, upright; height 30 cm (12 inches).
Growth: Vigorous; length between internodes — 2 to 2½ cm; much branched.
Canes: Slender; sturdy.
Main stems: Light olive green.
Branches: Medium green to light olive green.
Thorns: Needle declining.
New shoots: Reddish green.

The miniature rose plant and its flowers as herein described may vary in slight detail due to climatic, soil and cultural conditions under which the variety may be grown.

The following is claimed:

1. A new and distinct variety of miniature rose plant, hardy, dwarf, bushy, upright, much branched habit, substantially as illustrated and described, characterized by buds and flowers which are in a color hue similar to Thanksgiving (Hybrid Tea—Rose—U.S. Plant Pat. No. 2,524 — expired) and giving a coloring effect of Mars orange flowers with buds being of Mars orange tinted brown and resembling Sheri Anne (Miniature Rose—U.S. Plant Pat. No. 3,826) in form and size, having buds and flowers of a distinct and unusual appearance as compared to other miniature rose plants; said flowers being fully double, having unique cupped form; and further characterized by its vigor, abundant foliage and ease of propagation from softwood cuttings and by budding, and with an abundance of flowers.

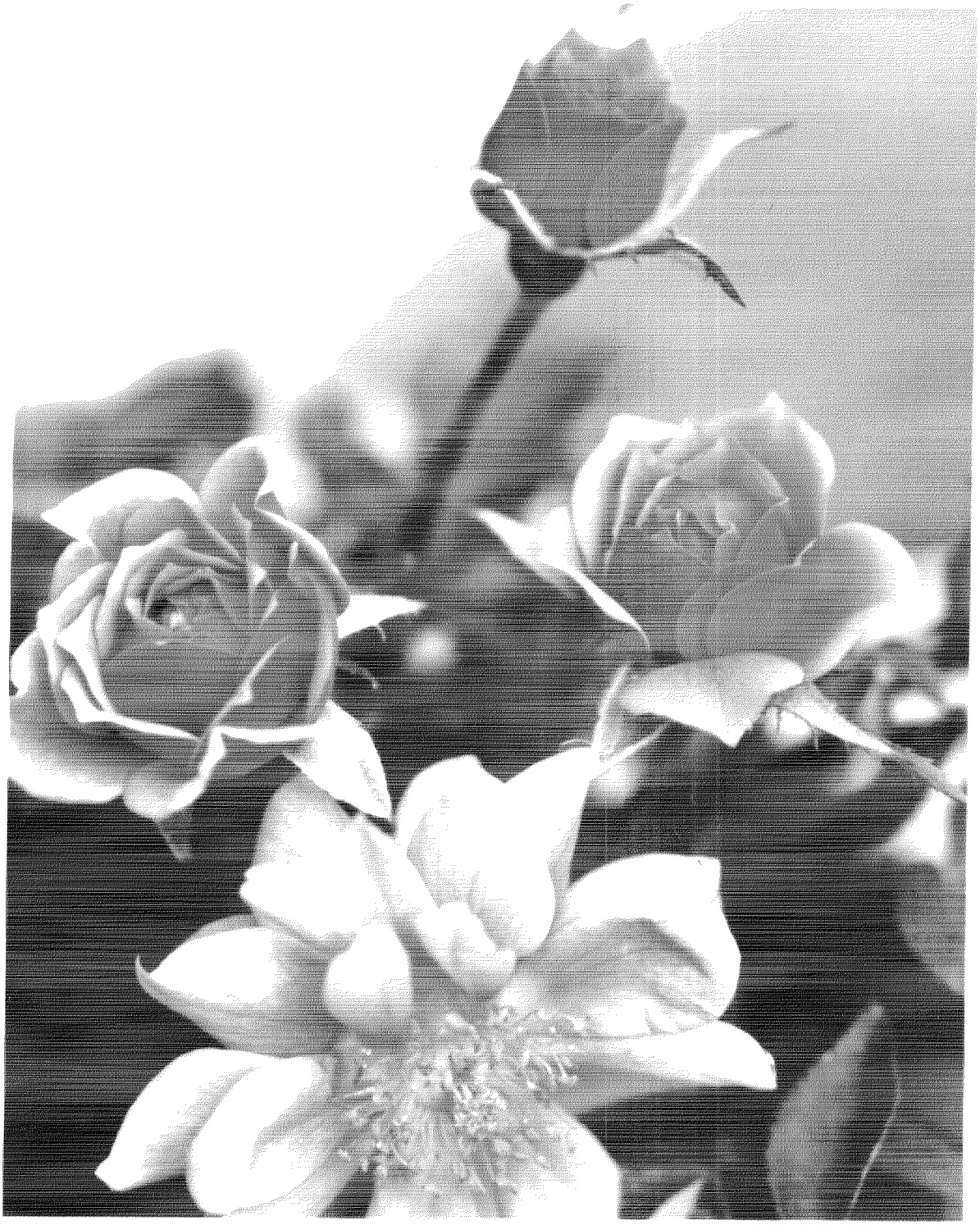

* * * * *